(12) United States Patent
Raz et al.

(10) Patent No.: US 6,884,213 B2
(45) Date of Patent: Apr. 26, 2005

(54) DEVICE AND METHOD FOR POSITIONING AN OBJECT IN A BODY LUMEN

(75) Inventors: Dan Raz, Haifa (IL); Arkady Glukhovsky, Santa Clarita, CA (US); Gavriel Meron, Petach Tikva (IL)

(73) Assignee: Given Imaging LTD, Yoqneam (IL)

( * ) Notice: Subject to any disclaimer, the term of this patent is extended or adjusted under 35 U.S.C. 154(b) by 0 days.

(21) Appl. No.: 10/322,772

(22) Filed: Dec. 19, 2002

(65) Prior Publication Data

US 2003/0139647 A1 Jul. 24, 2003

Related U.S. Application Data

(63) Continuation of application No. 09/577,381, filed on May 23, 2000, now abandoned.

(51) Int. Cl.[7] .................................................. A61B 1/00
(52) U.S. Cl. ....................................................... 600/104
(58) Field of Search ................................. 600/104, 156; 604/21, 514, 59, 60, 70, 72, 93.01, 95.02, 11, 13, 15, 57, 131, 150

(56) References Cited

U.S. PATENT DOCUMENTS

| | | |
|---|---|---|
| 4,278,077 A | 7/1981 | Mizumoto |
| 4,994,029 A | 2/1991 | Rohrbough |
| 5,304,123 A | 4/1994 | Atala et al. |
| 5,311,858 A | 5/1994 | Adair |
| 5,330,427 A | 7/1994 | Weissenberger |
| 5,604,531 A | 2/1997 | Iddan et al. |
| 5,643,677 A | 7/1997 | Feifer et al. |
| 5,653,677 A | 8/1997 | Okada et al. |
| 5,674,179 A | 10/1997 | Bonnet et al. |
| 5,681,279 A | 10/1997 | Roper et al. |
| 5,819,736 A | 10/1998 | Avny et al. |
| 5,827,175 A | 10/1998 | Tanaka |
| 5,904,647 A * | 5/1999 | Ouchi .......................... 600/104 |

FOREIGN PATENT DOCUMENTS

| | | |
|---|---|---|
| JP | 7275197 | 10/1995 |
| WO | WO 99/32028 | 7/1999 |

\* cited by examiner

*Primary Examiner*—Beverly M. Flanagan
(74) *Attorney, Agent, or Firm*—Pearl Cohen Zedek Latzer, LLP

(57) ABSTRACT

It is an object of the present invention to provide a device and method for controlled positioning and/or releasing an object in a body lumen.

The device of the invention comprises a liquid filled tube detachably connected to an injecting apparatus at its proximal end and to a holding and releasing unit having a bore configured to hold and release the object, at its distal end. The holding and releasing unit is connected to the tube such that liquid can pass from the tube into the holding and releasing unit bore.

The distal end of the tube is capable of being inserted and maneuvered through a body lumen.

The object is retained in the device during its manipulation through the body lumen due to frictional force exerted by the holding and releasing unit on the object. The object is released by activating the injecting apparatus to achieve an hydraulic pressure in the holding and releasing unit bore which is higher than the frictional force.

19 Claims, 4 Drawing Sheets

DEVICE AND METHOD FOR POSITIONING AN OBJECT IN A BODY LUMEN

RELATED APPLICATIONS

This application is a continuation of U.S. patent application Ser. No. 09/577,381, filed on May 23, 2000, now abandoned, of which this application is a continuation and which is incorporated in its entirety by reference herein.

FIELD OF THE INVENTION

The present invention relates to a device and method for positioning and releasing an object at a desired time and location in a body lumen.

BACKGROUND OF THE INVENTION

It is often desired to insert objects, such as surveillance probes or drugs into body lumens. These are usually inserted with the aid of endoscopes.

An endoscope is a device meant for viewing the interior of the body. Endoscopes typically consist of a tube and an optical system and are usually introduced through the mouth or anus for viewing parts of the gastrointestinal tract. Endoscopes are used to look directly at the outside of the uterus, Fallopian tubes, ovaries, appendix, and other abdominal organs. Other endoscopes are inserted through incisions to look at joints, and still others to view the inside of the bladder.

Endoscopes are also used for inserting objects into the body. Endoscopes having at their inserted end different shaped baskets for carrying objects are inserted into the body and the objects are released from the basket into the body lumen by controlled movements of the opposite end of the endoscope tube by an operator.

WO 99/32028, which is assigned to the common assignees of the present invention, describes a device for delivering an autonomous video capsule into the gastrointestinal tract. The device includes an endoscope having a clamp, which is held in the front of the endoscope by at least one support, for releasably holding the capsule.

In the known methods which utilize endoscopes for inserting and releasing objects in the body, the release of the object from the endoscope is a mechanical operation limited by factors such as the endoscope tube flexibility or the operator's proficiency. Also, as a result of the endoscope movements during its operation, there is a chance of loosing the object at an undesired location or at an undesired time.

The known methods, therefore, do not enable facile and precise positioning of or exact timing of release of objects in body lumens. Thus, there exists a need for a method and device which enable precise positioning of an object in a body lumen and which provide the operator with complete control over the positioning and timing of release of the object.

SUMMARY OF THE INVENTION

It is an object of the present invention to provide a device and method for positioning and/or releasing an object in a body lumen. The device and method of the invention enable precise positioning and/or release of an object by utilizing an hydraulic mechanism for releasing the object. Use of the device of the invention ensures that the object is retained during any desired portion of the device's course through the body lumen and that facile and controlled release of the object are possible at any chosen time.

The device of the invention comprises a liquid filled tube having a proximal end and a distal end; an injecting apparatus; and a holding and releasing unit having an bore configured to hold and release the object. The liquid filled tube is detachably connected at its proximal end to the injecting apparatus and detachably connected at its distal end to the holding and releasing unit, such that liquid can pass from the tube into the bore.

The distal end of the tube is capable of being inserted and maneuvered through a body lumen.

In an embodiment of the invention the tube of the device is inserted into an endoscope tube before being connected to the injecting apparatus and holding and releasing unit. The device is thus inserted, together with the endoscope, into a body lumen.

The injecting apparatus may be any apparatus suitable for injecting liquid through a tube. The injecting apparatus, which may be manually operated or under automatic control, is typically filled with liquid, typically the same liquid filling the tube, and is connected, preferably hermetically, to the proximal end of tube.

The holding and releasing unit is configured to hold and release an object desired to be inserted and/or released in the body at one end (the holding end) and for being connected, preferably hermetically, to the device tube at the other end (the connecting end). At its holding end the holding and releasing unit has a bore having an inner diameter that is compatible with the object perimeter, such that the object can be tightly fit into it. At its connecting end the holding and releasing unit is connected, preferably hermetically, to the distal end of the device tube such that liquid can pass from the tube into the holding and releasing unit's bore.

The object is retained in the holding and releasing unit due to frictional force. The object is released from the holding and releasing unit, for example when a desired location in the body lumen is reached, by hydraulic pressure achieved through the action of the injecting apparatus, which forces a volume of liquid from the device tube into the bore of the holding and releasing unit. This hydraulic pressure can be used not only to release but also to drive the object out of the holding and releasing unit.

The present invention further provides a method for positioning and/or releasing an object in a body lumen. The method comprises the steps of placing the object in the bore of the holding and releasing unit of the device of the invention; inserting the device into a body lumen; manipulating the holding and releasing unit to a desired location in the body lumen; and activating the injecting apparatus of the device to obtain hydraulic pressure in the bore of the holding and releasing unit, whereas the hydraulic pressure is such so as to release the object from the holding and releasing unit.

It will be appreciated that the distal end of the device tube, which is connected to the holding and releasing unit, is inserted into the body lumen, while the proximal end of the device tube, which is connected to the injecting apparatus, remains out side of the body lumen.

BRIEF DESCRIPTION OF THE DRAWINGS

The present invention will be understood and appreciated more fully from the following detailed description taken in conjunction with the appended drawings in which.

DETAILED DESCRIPTION OF THE INVENTION

The present invention relates to a device and method for precisely positioning and/or releasing an object in a body lumen. The method utilizes a device for holding and releasing the object. The device, part of which is inserted into the body lumen, retains the object due to frictional force exerted on the object. The object is released from the device by applying hydraulic pressure which overcomes the force retaining the object.

Figure 1:
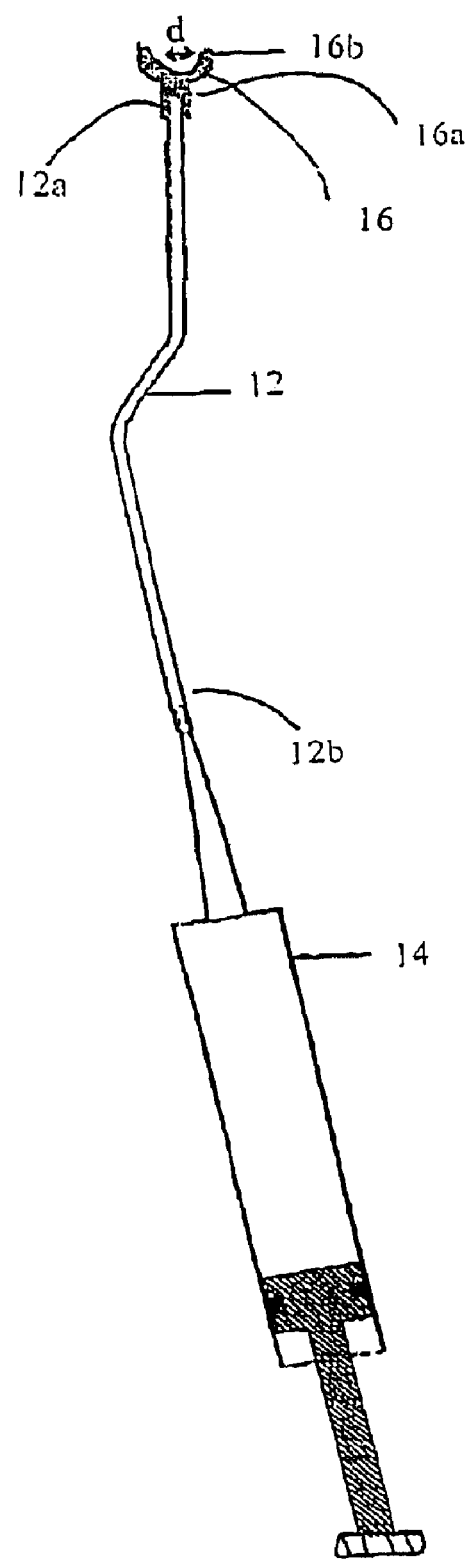
FIG. 1 is a schematic cross section illustration of the device according to an embodiment of the invention.

Reference is now made to FIG. 1 in which an embodiment of the device of the invention is schematically illustrated. The device of the invention comprises a tube 12, detachably connected to an injecting apparatus 14 at one end (the proximal end 12b) and to a holding and releasing unit 16 at the other end (the distal end 12a).

Tube 12 is both flexible and rigid enough to be inserted and pushed through a body lumen while following the body lumen contours. Prior to being inserted into a body lumen tube 12 is filled with water or any other suitable liquid and is connected to injecting apparatus 14 at its proximal end (the end which is accessible to an operator) and to holding and releasing unit 16 at its distal end (the end which is inserted into the body).

Injecting apparatus 14 may be any apparatus suitable for injecting liquid through tube 12, such as a syringe, pump etc. Injecting apparatus 14, which may be manually operated or under automatic control, can be filled with liquid, typically the same liquid filling tube 12, and is connected, preferably hermetically, to the proximal end of tube 12.

Holding and releasing unit 16 is configured for holding an object desired to be inserted and/or released into a body lumen at one end (the holding end 16b) and for being connected to tube 12 at the other end (the connecting end 16a). At its holding end 16b holding and releasing unit 16 comprises a bore having an inner diameter d which is compatible with the object perimeter, such that the object can be tightly fit into it. Holding and releasing unit 16 is made of a material having a high friction coefficient, preferably an elastic plastic such as polyurethane.

The mechanism of securely retaining and of timely releasing an object from the holding and releasing unit 16 is described in connection with FIGS. 2A–3.

The device of the invention may be inserted into a body lumen on its own or together with any other device suitable for being inserted into a body lumen.

Figure 2A:
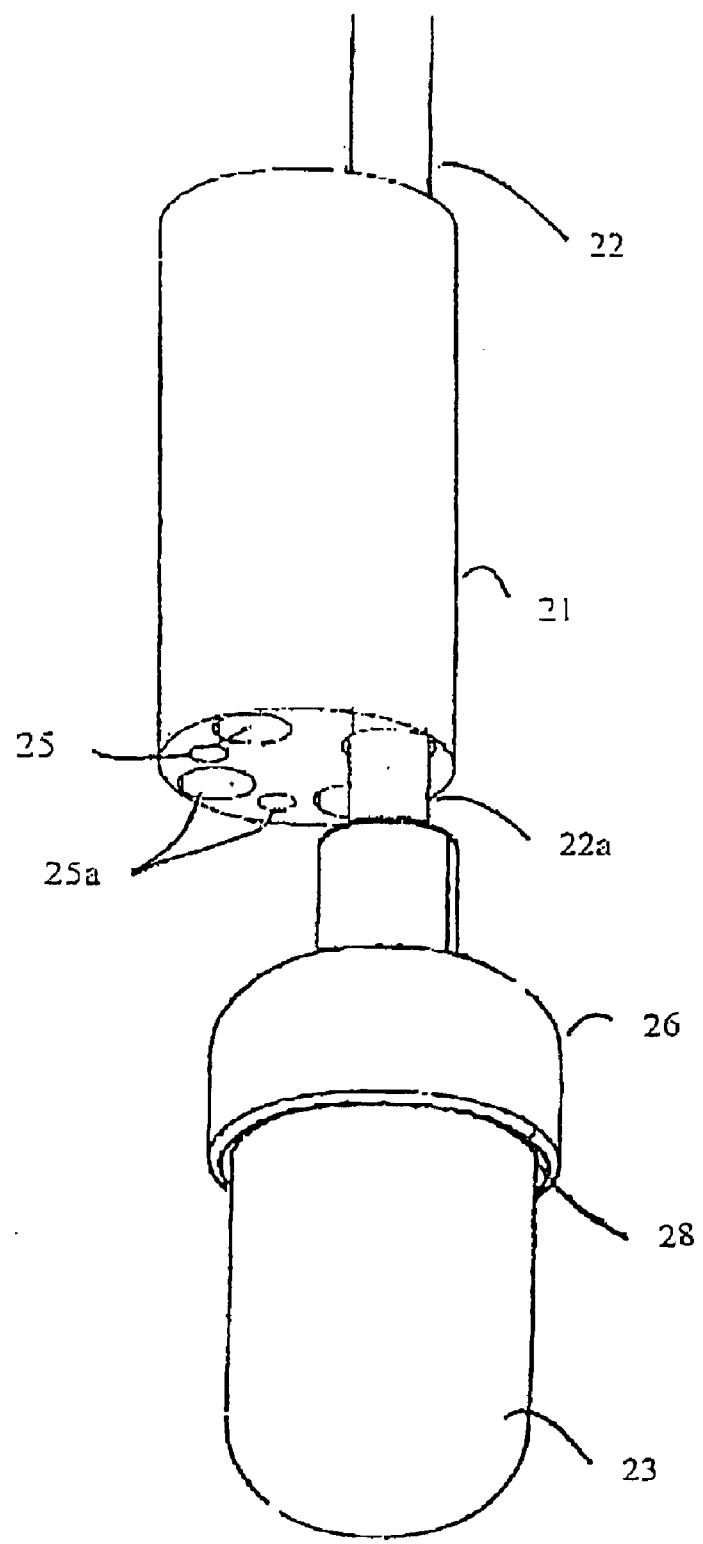
FIGS. 2A and 2B are, respectively, a schematic overview illustration and a more detailed cross section illustration of the device and endoscope according to an embodiment of the invention.
Figure 2B:
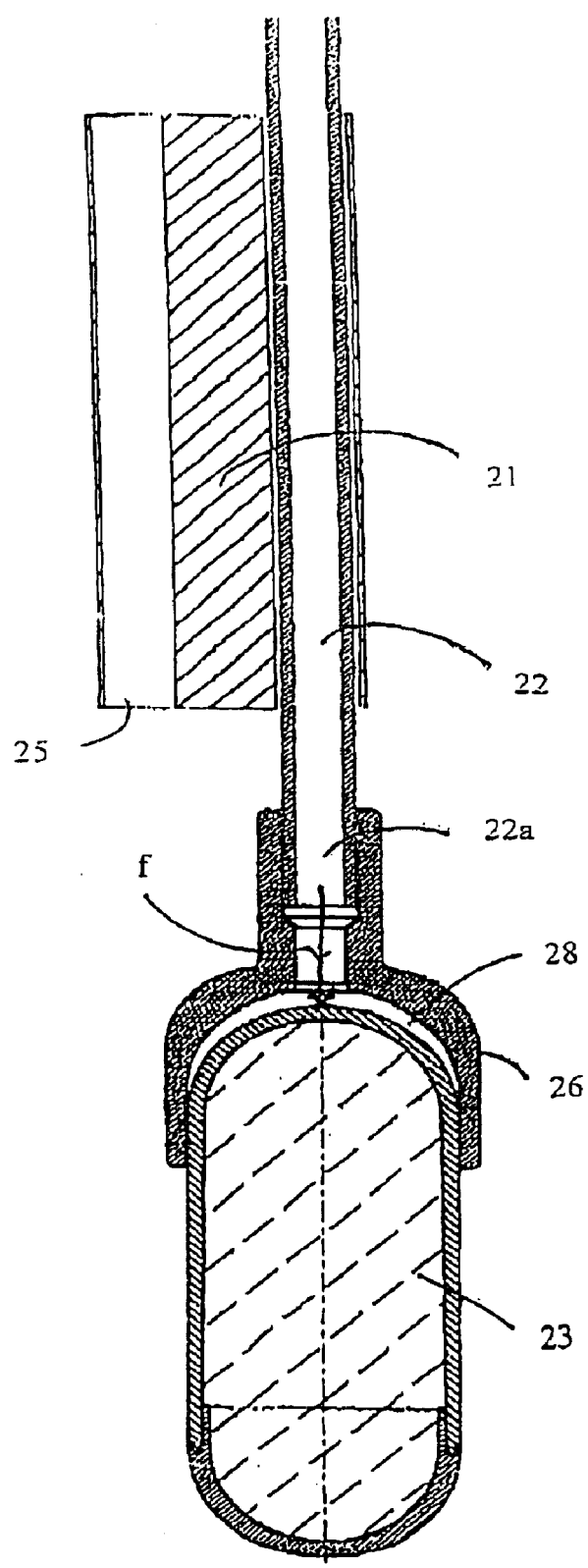
Figure 3:
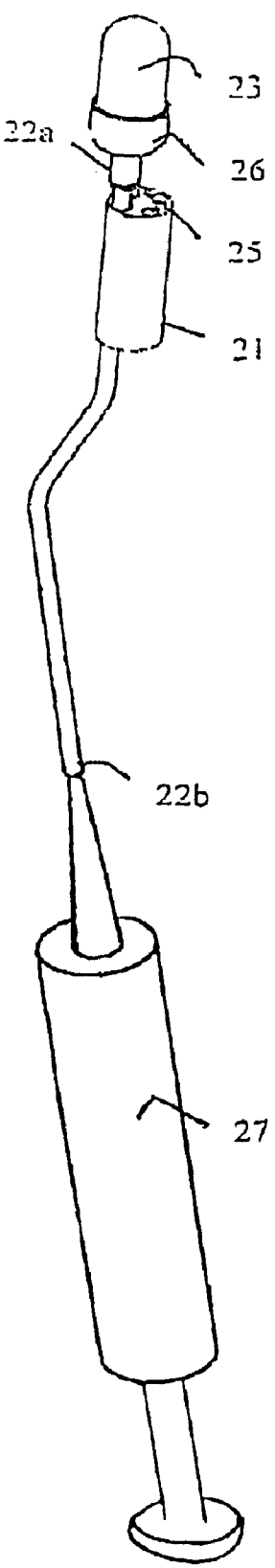
FIG. 3 is a schematic illustration of a device and endoscope operable according to the invention.

In an embodiment of the invention, illustrated in FIGS. 2A–3, the device is inserted into a body lumen together with an endoscope.

As shown in FIGS. 2A, 2B and 3, tube 22 is inserted through a channel in an endoscope tube (a section of which is shown as endoscope tube 21) such that its proximal end (22b in FIG. 3) and distal end 22a protrude from endoscope tube 21 Tube 22 is both flexible and rigid enough to be inserted and freely pushed or pulled through a channel in the endoscope tube 21 and to follow the endoscope tube course through a body lumen. After being inserted through the endoscope tube 21 tube 22 is filled with water or any other suitable liquid and is connected to injecting apparatus 27 at its proximal end 22b and to the holding and releasing unit 26 at its distal end 22a. Holding and releasing unit 26 is connected to distal end 22a such that liquid can pass from tube 22 into the holding and releasing unit's bore 28. The passage of liquid from tube 22 into the holding and releasing unit's bore 28 is illustrated by arrow f in FIG. 2B.

Before the endoscope tube 21 is inserted into the body, an object 23 is fit into the holding and releasing unit's bore 28. Tube 22 is filled with an appropriate liquid either before or after holding and releasing unit 26 is connected to distal end 22a, but prior to fitting object 23 into bore 28, and an injecting apparatus 27 is connected, preferably hermetically, to the proximal end 22b of tube 22.

The endoscope tube 21 may carry additional functional units necessary for the endoscope operation. For example, a viewing or imaging device may be inserted through channel 25 while wires supplying energy for the viewing or imaging device are inserted through any of channels 25a. Thus, both a viewing or imaging device and an object can be simultaneously carried into a body lumen. The endoscope tube 21 carrying the device of the invention and any additional functional units is inserted into a body lumen and manipulated to a desired location in the body lumen. Determining the location desired for positioning or releasing the object 23 can be aided, for example, by using a viewing device which is carried by endoscope tube 21.

The object 23 is retained in the holding and releasing unit 26 due to the frictional force exerted by the holding and releasing unit 26. The force retaining object 23 must be sufficient to hold the object 23 throughout the passage of the device through the body lumen until a desired location is reached. The force exerted on the object 23 (the holding force) is equal to the force exerted by the bore 28 walls times the friction coefficient of the bore 28 wall material. Thus, the material and measurements of the holding and releasing unit 26 should be such to achieve a holding force which exceeds the forces typically exerted on the object 23 during the passage of the endoscope through the body lumen, such as friction of the object with the body lumen walls, acceleration of the endoscope tube etc.

When a desired location is reached object 23 may be released from the holding and releasing unit 26. Object 23 is released from the holding and releasing unit 26 by a volume of liquid that is forced from tube 22 into bore 28 through the action of injecting apparatus 27. Liquid forced into bore 28 by the injecting apparatus 27 infiltrates in between the bore's 28 inner walls and the object 23 perimeter, thereby reducing the friction coefficient and enabling object 23 to be easily released from holding and releasing unit 26. The object 23, which is released into the body lumen in the direction taken by the endoscope, is being driven out of the holding and releasing unit 26 by a releasing force which is equal to the pressure of the volume of liquid forced by injecting apparatus 27 times the object surface area which occupies the holding and releasing unit. Thus, the volume of liquid being forced by injecting apparatus 27 may be calculated to accommodate for the required releasing force.

After the release of object 23 the endoscope may be removed from the body or the endoscope may be used, for example by utilizing a viewing device, to view or follow the course of the object 23 in the body lumen.

Objects to be inserted and/or released in the body may include probes for surveillance of the interior of the body, such as a swallowable capsule comprising a data collecting system, such as imaging or sensing systems and systems for transmitting the collected data. Objects desired to be inserted and/or released in the body may also include drugs, sample collecting devices etc. These objects can be tailored to fit the holding and releasing unit 26 measurements or the holding and releasing unit 26 can be designed to fit a specific object so that the object closely fits the holding and releasing unit 26 such that hydraulic pressure can be achieved for releasing the object as described above.

It will be appreciated by persons skilled in the art that the present invention is not limited to what has been particularly shown and described hereinabove.

Rather the scope of the present invention is defined only by the claims which follow:

1. A device for positioning an object in a body lumen, the device comprising:
   a holding and releasing unit having a bore configured to hold the object, and to release the object by hydraulic pressure;
   a liquid filled tube having a proximal end and a distal end; and an injecting apparatus;
wherein the liquid filled tube is detachably connected at its proximal end to the injecting apparatus and detachably connected at its distal end to the holding and releasing unit, such that liquid can pass from the tube into the bore, and
wherein the distal end of the tube is capable of being inserted and maneuvered through a body lumen.

2. A device according to claim 1, wherein the tube is capable of being inserted and maneuvered through an endoscope tube so as to follow the endoscope tube course through a body lumen.

3. A device according to claim 1, wherein the injecting apparatus is hermetically connected to the proximal end of the tube.

4. A device according to claim 1, wherein the injecting apparatus is filled with liquid.

5. A device according to claim 4 wherein the injecting apparatus is filled with the same liquid as the tube.

6. A device according to claim 1, wherein the tube is filled with water.

7. A device according to claim 1, wherein the holding and releasing unit comprises:
a holding end having a bore for holding and releasing the object; and
a connecting end for connecting to the tube,
and wherein the holding end is hermetically connected to the distal end of the tube.

8. A device according to claim 7 wherein the bore has an inner diameter that is compatible with an object perimeter, such that the object can be tightly fit into the bore.

9. A device according to claim 1 wherein the holding and releasing unit is made of a material having a high friction coefficient.

10. A device according to claim 9 wherein the material is polyurethane.

11. A device according to claim 1 wherein the object is selected from the group consisting of probes for surveillance of the interior of the body, drugs and sample collecting devices.

12. A method for positioning an object in a body lumen using a device including a holding and releasing unit with a bore and an injecting apparatus for injecting liquid into the bore, the method comprising the steps of:
placing the object in the bore of the holding and releasing unit of the device;
holding the object in the bore via a friction fit;
inserting the device into a body lumen;
manipulating the holding and releasing unit to a desired location in the body lumen; and
activating the injecting apparatus of the device to obtain hydraulic pressure in the bore of the holding and releasing unit, wherein the hydraulic pressure is such so as to release the object from the holding and releasing unit.

13. A method according to claim 12, wherein during the step of manipulating the holding and releasing unit to a desired location a frictional force is exerted by the holding and releasing unit on the object so as to retain the object and wherein during the step of activating the injecting apparatus, the hydraulic pressure obtained achieves a force that is higher than the frictional force.

14. A method according to claim 12 wherein the object is selected from the group consisting of probes for surveillance of the interior of the body, drugs and sample collecting devices.

15. A device for positioning or releasing an object in a body lumen, the device comprising:
a liquid filled tube having a proximal end and a distal end;
an injecting apparatus;
a holding and releasing unit having a bore configured to hold the object, and to release the object using hydraulic pressure; and
wherein the liquid filled tube is detachably connected at its proximal end to the injecting apparatus, wherein liquid can pass from the tube into the bore.

16. A device for positioning an object in a body lumen, the device comprising:
a liquid filled tube having a proximal end and a distal end;
an injecting apparatus;
a holding and releasing unit having a bore configured to hold the object, and to release the object using hydraulic pressure; and
wherein the liquid filled tube is detachably connected at its distal end to the holding and releasing unit, such that liquid can pass from the tube into the bore.

17. A method for positioning an object in a body lumen using a device including a holding and releasing unit with a bore, a liquid filled tube detachably connected at its proximal end to an injecting apparatus for injecting liquid into the bore, the method comprising the steps of:
placing the object in the bore of the holding and releasing unit of the device;
inserting the device into a body lumen;
manipulating the holding and releasing unit to a desired location in the body lumen; and
activating the injecting apparatus of the device to obtain hydraulic pressure in the bore of the holding and releasing unit, wherein the hydraulic pressure is such so as to release the object from the holding and releasing unit.

18. A method for positioning and releasing an object in a body lumen, the method comprising the steps of:
placing the object in the bore of the holding and releasing unit of the device according to claim 1;
inserting the device into a body lumen;
manipulating the holding and releasing unit to a desired location in the body lumen; and
activating the injection apparatus of the device according to claim 1 to obtain hydraulic pressure in the bore of the holding and releasing unit, wherein the hydraulic pressure is such so as to release the object from the holding and releasing unit;
wherein during the step of manipulating the holding and releasing unit to a desired location a frictional force is exerted by the holding and releasing unit on the object so as to retain the object and wherein during the step of activating the injection apparatus, the hydraulic pressure obtained achieves a force that is higher than the frictional force.

19. A device for positioning an object in a body lumen, the device comprising:
a holding and releasing unit having a bore configured to hold the object by a friction fit and to release the object by hydraulic pressure;
a liquid filled tube having a proximal end and a distal end; and an injecting apparatus;
wherein the liquid filled tube is detachably connected at its proximal end to the injecting apparatus and detachably connected at its distal end to the holding and releasing unit, such that liquid can pass from the tube into the bore, and wherein the injecting apparatus is filled with liquid.

* * * * *